(12) United States Patent
Kaneki et al.

(10) Patent No.: US 7,545,500 B2
(45) Date of Patent: Jun. 9, 2009

(54) SURFACE PLASMON RESONANCE PHENOMENON MEASURING EQUIPMENT

(75) Inventors: Noriaki Kaneki, Hokkaido (JP); Toshihiko Imato, Fukuoka (JP); Akihide Hemmi, Tokyo (JP); Katsumi Uchiyama, Tokyo (JP); Yasukazu Asano, Saitama (JP); Kouji Shimada, Hokkaido (JP)

(73) Assignees: Muroran Institute of Technology, Mizumoto-cho, Muranran-shi, Hokkaido (JP); Kyushu University, National University Corp., Hakozaki, Higashi-ku, Fukuoka-shi, Fukuoka (JP); Meblus Advanced Technology Ltd., Nishiogi-kita, Suginami-ku, Tokyo (JP)

( * ) Notice: Subject to any disclaimer, the term of this patent is extended or adjusted under 35 U.S.C. 154(b) by 0 days.

(21) Appl. No.: 11/570,654

(22) PCT Filed: Jun. 17, 2005

(86) PCT No.: PCT/JP2005/011569

§ 371 (c)(1),
(2), (4) Date: Dec. 14, 2006

(87) PCT Pub. No.: WO2005/124318

PCT Pub. Date: Dec. 29, 2005

(65) Prior Publication Data

US 2008/0291453 A1    Nov. 27, 2008

(30) Foreign Application Priority Data

Jun. 17, 2004    (JP)    ............................... 2004-179841

(51) Int. Cl.
    *G01N 21/55* (2006.01)
(52) U.S. Cl. .................................................. 356/445

(58) Field of Classification Search ....................... None
    See application file for complete search history.

(56) References Cited

U.S. PATENT DOCUMENTS 5,563,707 A * 10/1996 Prass et al. .................. 356/517

(Continued)

FOREIGN PATENT DOCUMENTS

JP    1 110352 U    7/1989

(Continued)

*Primary Examiner*—Gregory J Toatley, Jr.
*Assistant Examiner*—Juan D Valentin

(57) ABSTRACT

The present invention discloses surface plasmon resonance phenomenon measuring equipment comprising:
(1) a prism,
(2) a sensor wherein a plurality of measuring cells are formed in m rows and n columns on the bottom face of the prism,
(3) a light source for radiating a laser beam,
(4) a first optical system wherein m optical units each having a rectangular parallelepiped shape and having a translucent film formed along the diagonal surface of the rectangular parallelepiped are arranged continuously,
(5) a second optical system wherein mn optical units are arranged continuously and a reflected lights group is radiated toward the measuring cells,
(6) a photodiode array detectors group of m rows and n columns, arranged on the extensions of reflected lights group, and
(7) a polarizer interposed between the first optical system and the prism, and/or between the prism and the photodiode array detectors.

4 Claims, 9 Drawing Sheets

U.S. PATENT DOCUMENTS

| | | | |
|---|---|---|---|
| 5,583,643 A * | 12/1996 | Gass et al. | 356/445 |
| 6,268,125 B1 * | 7/2001 | Perkins | 356/320 |
| 6,432,364 B1 * | 8/2002 | Negami et al. | 422/82.11 |
| 6,545,276 B1 * | 4/2003 | Sasaki | 382/130 |
| 6,623,977 B1 * | 9/2003 | Farquharson et al. | 356/301 |
| 2001/0026943 A1 | 10/2001 | Dickopf | |
| 2002/0001085 A1 | 1/2002 | Dickopf | |

FOREIGN PATENT DOCUMENTS

| | | |
|---|---|---|
| JP | 8 5547 A | 1/1996 |
| JP | 11 132944 A | 5/1999 |
| JP | 2001 255267 A | 9/2001 |
| JP | 2002 71555 A | 3/2002 |
| JP | 3335621 | 8/2002 |
| JP | 3356212 | 10/2002 |
| JP | 3462179 | 8/2003 |

\* cited by examiner

SURFACE PLASMON RESONANCE PHENOMENON MEASURING EQUIPMENT

TECHNICAL FIELD

The present invention relates to multi-channel surface plasmon resonance phenomenon measuring equipment wherein a plasmon resonance phenomenon is utilized as a principle of measurement and simultaneous analysis of a plurality of samples can be made.

BACKGROUND ART

Surface plasmon resonance phenomenon measuring equipment is an apparatus which enables the monitoring of food safety or environment or the high-sensitivity detection of dangerous articles or drugs. This equipment is expected to find applications in a number of fields such as environmental protection, medical care, agriculture, stock raising, food industry and the like.

Surface plasmon resonance (SPR) measuring equipment has been marketed by BIACORE AB, NIPPON LASER & ELECTRONICS LAB, etc. With these equipment, the number of samples measured at one time is one, making low the efficiency of measurement.

In order to make small the SPR measuring equipment to enable on-site measurement, the present inventors developed portable SPR sensors (Japanese Patent No. 3462179, No. 3335621 and No. 3356212) wherein a light radiated from a light source is passed through a cylindrical lens to form a liner focus, the light of linear focus is allowed to be incident on a sensor made of a prism and a glass substrate, and the reflected light from the prism is measured by a CCD linear sensor. Even with these measuring equipment, the number of samples measured at one time is one as well, making low the efficiency of measurement.

In order to increase the efficiency of measurement, there is required a function enabling simultaneous analysis of a large number of samples, i.e. a function of simultaneous measurement of multi-sample or multi-channeling.

There are two proposals for realizing the multi-channeling. The first proposal is an approach in which a light from a light source is divided into two light paths by a beam splitter, they are allowed to hit the pre-determined two points of a SPR sensor constituted by a prism, the attenuated lights caused by surface plasma resonance phenomenon are detected by two independent light detectors, then the detection signals are each amplified (Japanese Patent No. 3462179). The second proposal is an approach in which a reflected light from a prism is divided into two light paths by a light-splitting mirror and they are detected by respective light detectors (Japanese Patent Application No. 2003-118565).

With the multi-channeling by these approaches, however, the division into light paths is one-dimensional (linear) and the number of samples measured at one time is limited to about two. Therefore, a striking increase in the efficiency of measurement is impossible.

Hence, it is desired to develop surface plasmon resonance phenomenon measuring equipment which has a function of efficiently analyzing a large number of samples (e.g. four or more samples) at one time, i.e. a function of simultaneous measurement of multi-sample or multi-channeling.

DISCLOSURE OF THE INVENTION

The present inventors made a study in order to solve the above-mentioned problems. As a result, the present inventors devised a beam splitter for converting a laser beam as a light source into a large number of parallel lights and, by utilizing the beam splitter, enabled simultaneous measurement of multi-sample.

The present invention has been completed based on the above finding. The present invention aims at providing surface plasmon resonance phenomenon measuring equipment which utilizes a surface plasmon resonance phenomenon (SPR) and achieves multi-channel measurement of multi-sample.

The present invention, which has achieved the above aim, is described below.

[1] Surface plasmon resonance phenomenon measuring equipment comprising:
  (1) a prism,
  (2) a sensor wherein a plurality of measuring cells are formed in m rows (m≧2) and n columns (n≧2) on a metal film formed on the bottom face of the prism,
  (3) a light source for radiating a laser beam,
  (4) a first optical system wherein m optical units each having a rectangular parallelepiped shape and having a translucent film formed along the diagonal surface of the rectangular parallelepiped are arranged continuously in the direction of the laser beam radiated from the light source and thereby the laser beam is converted into a transmitted light and a m parallel reflected lights A group,
  (5) a second optical system fitted to one side of the prism, wherein optical units same as said m optical units are arranged in n columns continuously along the radiation directions of the m parallel reflected lights of said parallel reflected lights A group and thereby the parallel reflected lights A group is converted into transmitted lights and a mn parallel reflected lights group B, and wherein the reflected lights group B is radiated toward the mn measuring cells on the metal film formed on the bottom face of the prism, so as to hit the metal film at an incident angle including the plasmon resonance angle and thereby a reflected lights C group is radiated from other side of the prism,
  (6) a photodiode array detectors group of m rows and n columns, arranged on the extensions of the reflected lights C group, and
  (7) a polarizer interposed between a beam splitter comprising the first optical system and the second optical system and the prism, and/or between the prism and the photodiode array detectors group.

[2] Surface plasmon resonance phenomenon measuring equipment according to [1], wherein each optical unit converts 90.00 to 99.99% of the luminous energy of the light incident thereon, into a transmitted light and 0.01 to 10.00% of the luminous energy into a reflected light.

[3] Surface plasmon resonance phenomenon measuring equipment according to [1], which comprises an operation means for memorizing the luminous energies of reflected lights C group in blank measurement when no sample is placed in the sensor, to correct the luminous energies of reflected lights C group in sample measurement.

[4] An optical apparatus for surface plasmon resonance phenomenon measuring equipment, which comprises:
  a beam splitter having:
    a first optical system wherein m optical units each having a rectangular parallelepiped shape and having a translucent film formed along the diagonal surface of the rectangular parallelepiped are arranged continuously in the radiation direction of the laser beam radiated from the light source and thereby the laser beam is converted into a transmitted light and a m parallel reflected lights A group, and a second optical system wherein optical units same as said m optical units are arranged in n columns continuously along the radiation directions of the m reflected lights of said parallel radiated lights A group and thereby the parallel reflected lights are converted into transmitted lights and mn parallel reflected lights B group, photodiode array detectors of m rows and n columns, and a connecting member for connecting the beam splitter and the photodiode array, wherein the connecting member has a means for changing the angle and distance formed by and between the beam splitter and the photodiode.

In the present invention, a laser beam is divided into desired (m×n) laser beams by a beam splitter. As a result, the light paths of the reflected lights group B radiated onto measuring cells become two-dimensional (planar in m rows and n columns) and, correspondingly therewith, the photodiode array detectors group receiving the reflected lights radiated from the measuring cells become as well two-dimensional (planar in m rows and n columns). Consequently, the number of samples measured at one time can be increased strikingly, elevating the efficiency of measurement. Further, despite of simultaneous measurement of a number of samples, the size of measuring equipment can be made compact.

In the present invention, the intensities of lights after laser beam splitting by the beam splitter are different from each other; however, this difference can be corrected by conducting an operation at the amplifier section or the CPU. When there is provided, like this, an operation means for correction of the luminous energies of reflected lights C group in sample measurement, a more accurate measurement result can be obtained.

The optical system used in the present invention is superior in scalability, and all the optical elements from light source to prism and detector can be used by scaling-up or scaling-down. By scaling down the optical elements and combining them with micro-cells, a palm-sized SPR system can be manufactured; or, by scaling up, there can be manufactured a SPR system using a plate of 96 holes as measurement cells, which is equivalent to commercial SPR systems.

In the present invention, since no lens is used for convergence of light paths, the manufacturing cost of measuring equipment can be made low and the measuring equipment per se can be made compact.

In the measurement utilizing a surface plasmon resonance phenomenon, it is necessary to change the angle of SPR excitation light and the angle of SPR reflected light depending upon the intended application. This necessity can be satisfied by preparing a plurality of prisms different in angle and selecting an optimum prism from them so as to meet the intended purpose. Further, by providing a mechanism with which the beam splitter unit and the detector unit are automatically arranged and adhered so as to match the angle of prism, a prism can be fitted into an optical system by a simple operation.

100 is a light source; 110 is a laser beam; 200 is a beam splitter; 210 is a first optical system; 220 is a second optical system; 230 is a parallel reflected lights A group; 240 is a parallel reflected lights B group; 250 is a translucent film; 260 is a translucent film; 300 is a sensor; 310 is a glass plate; 320 is a metal film; 330 is a measuring cell; 340 is a reflected lights C group; 410 is a prism; 420a is a polarizer; 420b is a polarizer; 500 is a detector; 510 is a photodiode array detectors group; 710 is a rotation axis of beam splitter; 720 is a rotation axis of detector; 730 is a guide bar; 732 is a long hole; 810 is a glass plate; 820 is a translucent film; 830 is an adhesive layer; A is a splitting unit of first optical system; A1 to Am are a splitting units group of first optical system; B is a splitting unit of second optical system; B11 to B1n ... Bm1 to Bmn are a splitting units group of second optical system; LA1 is a reflected light from a splitting unit A1; LAm is a reflected light from a spitting unit Am; LB1n is a reflected light from a splitting unit B1n; LBm1 is a reflected light from a splitting unit Bm1; LBmn is a reflected lights group from a splitting units group BmN; θa is an incidence angle; and θb is a reflection angle.

BEST MODE FOR CARRYING OUT THE INVENTION

The present invention is described in detail below with reference to the accompanying drawings.

Figure 1:
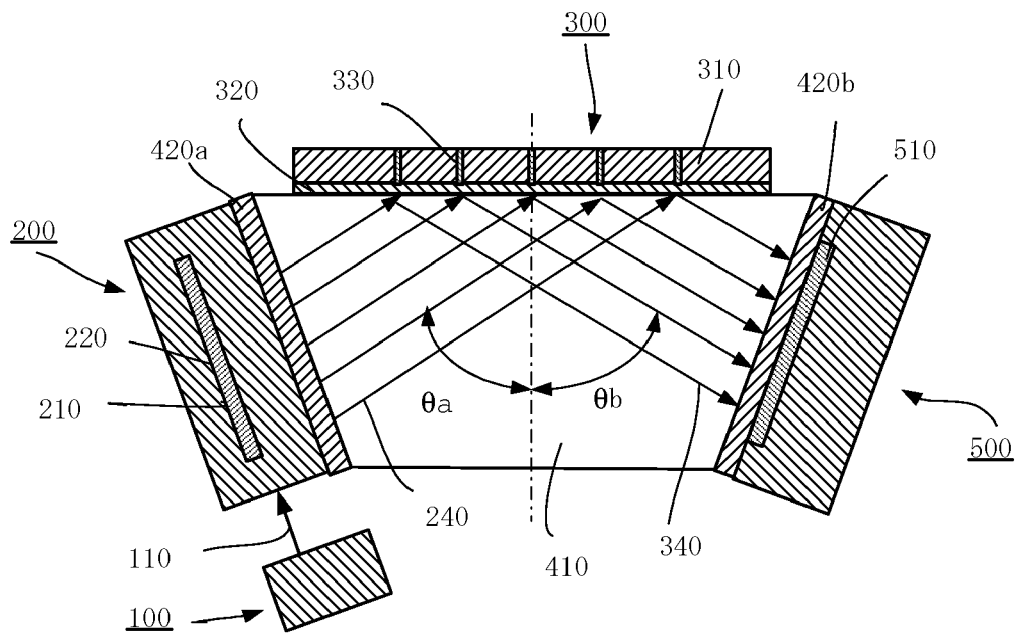
FIG. 1 is a schematic view showing an example of the surface plasmon resonance phenomenon measuring equipment of the present invention.

FIG. 1 is a plan view showing an example of the surface plasmon resonance phenomenon measuring equipment of the present invention. In FIG. 1, 100 is a light source; 200 is a beam splitter; 300 is a sensor; 410 is a prism; and 500 id a detector.

In FIG. 1, a laser beam 110 is radiated from the light source 100 toward the beam splitter 200. In the beam splitter 200, the laser beam 110 is transmitted through the splitting units A1 to Am (described later) of first optical system 210 in this order.

When the laser beam 110 is transmitted, part of the transmitted light is separated by the splitting units A1 to Am and becomes a parallel reflected lights A group 230 (described later); and these reflected lights are transmitted through respective corresponding splitting units of B11 to B1n . . . Bm1 to Bmn (described later) of second optical system 220 in this order. When the parallel reflected lights A group are transmitted through the splitting units B11 to Bmn, part of each transmitted light is separated and becomes a parallel reflected lights B group 240. The parallel reflected lights B group 240 passes through a polarizer 420a and then through the prism 410 and is incident on the surface of metal film 320 formed on the surface of sensor 300, at an incidence angle θa.

The incidence angle θa of each reflected light on the sensor is an incidence angle including the plasmon resonance angle. The incidence position of each of the parallel reflected lights B group 240 is the surface position of the metal film 320 right beneath the corresponding measuring cell (one of measuring cells of m rows and n columns).

300 is a sensor which is a glass plate 310 having a metal film 320 vapor-deposited on the bottom surface. The sensor 300 is mounted on the upper surface of prism 410 via a matching plate not shown in FIG. 1. On the upper surface of the metal film 320 of the sensor 300 are formed a plurality of measuring cells 330 (described later) of m rows and n columns.

From the metal film 320 right beneath the measuring cells 330, on which the parallel reflected lights B group 240 is incident, there is radiated, at a reflection angle θb, a reflected lights C group 340 (each sample in each measuring cell gives a different angle of resonance owing to surface plasmon resonance phenomenon and, as a result, different reflected lights C are radiated from different samples). The reflected lights C group 340 passes through the prism 410 and then through a polarizer 420b, is incident simultaneously on each corresponding position of the photodiode array detectors group 510 (of m rows and n columns) in the detector 500. The photodiode array detectors group 510 detects each SPR signal image generated by each measuring cell (of m rows and n columns) of the sensor 300, as an independent light spot.

Figure 2:
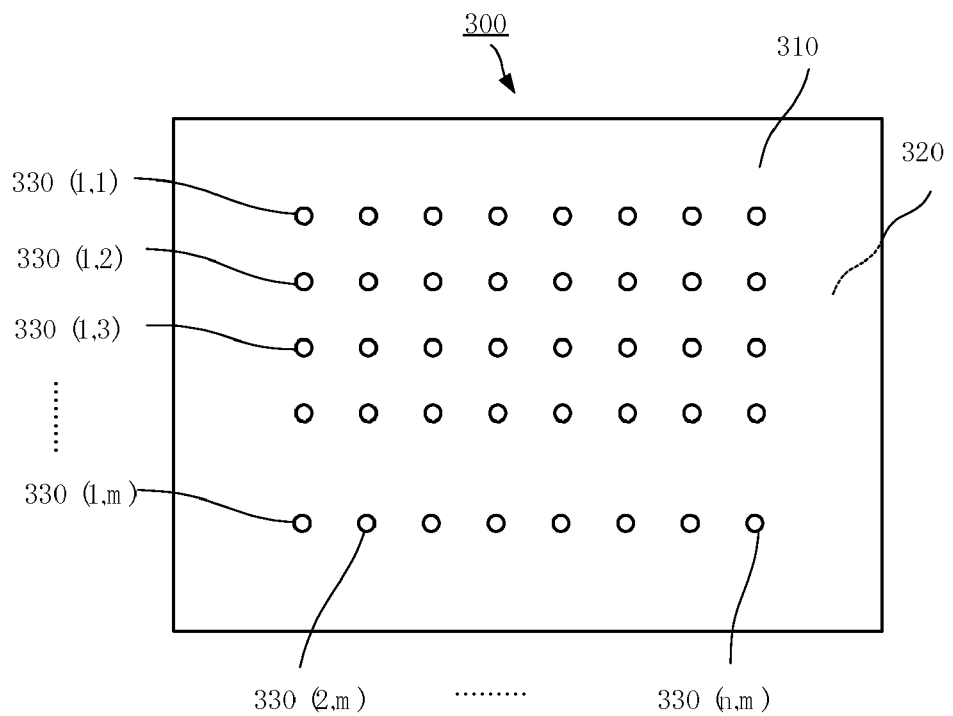
FIG. 2 is a view showing the position relationship of the measuring cells in sensor.

FIG. 2 is a plan view of a sensor 300, wherein measuring cells arranged two-dimensionally in m rows and n columns, i.e. 330 (1, 1), 330 (1, 2), 330 (1, n) . . . 330 (m, n) are formed on a metal film 320.

Figure 3:
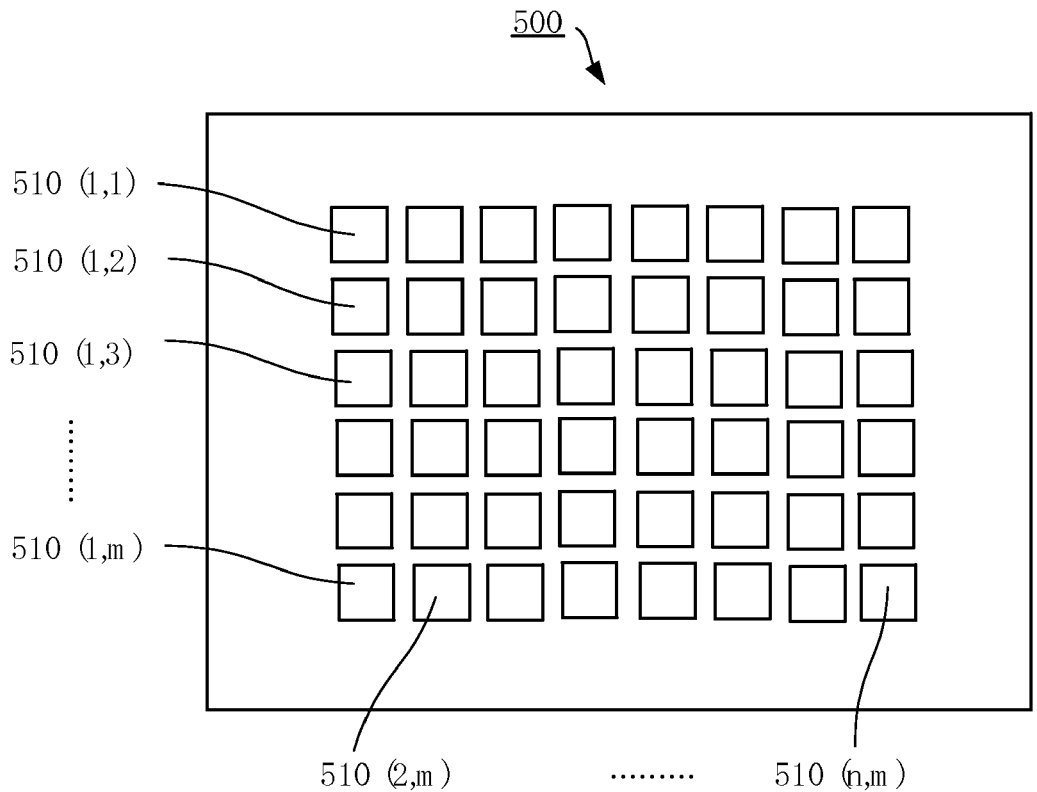
FIG. 3 is a view showing the position relationship of the photodiode array detectors group in detector.

FIG. 3 is a plan view showing the photodiode array detectors group 510 of detector 500, and the photodiode array detectors group 510 is constituted by photodiode array detectors arranged two dimensionally in m rows and n columns. The detector 500 per se is known and being marketed.

Figure 4:
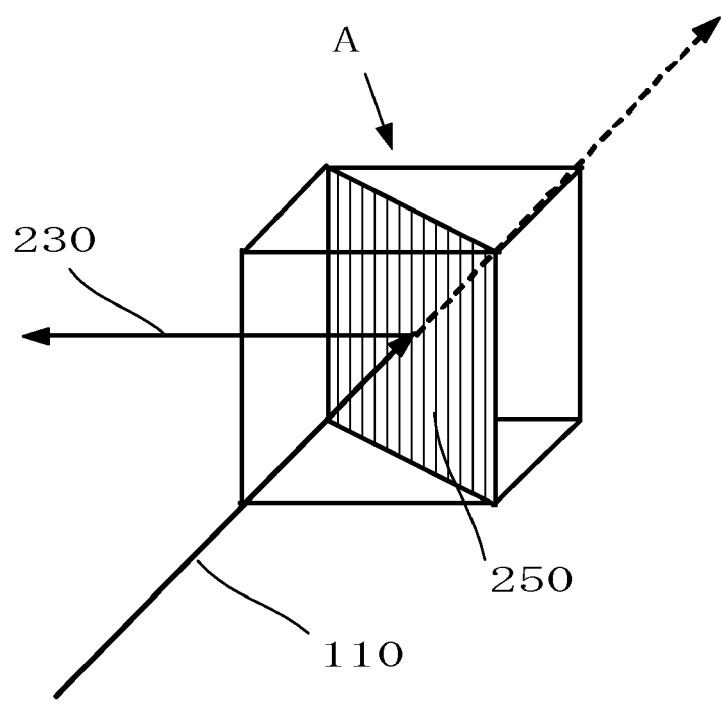
FIG. 4 is a perspective view showing an example of the splitting unit of first optical system.

FIG. 4 is a perspective showing a unit A constituting the splitting units group A1 to Am of first optical system 210. In FIG. 4, 250 is a translucent film which is provided along one diagonal surface of the transparent rectangular parallelepiped constituting the unit. This translucent film 250 functions as a half mirror and is constituted by, for example, a single-layer or multi-layer dielectric film, a thin metal film or a hybrid film thereof. The translucent film 250 is constituted by a film causing no optical deflection and separates part of an incident laser beam 110 as a reflected light 230. The first optical system 210 described later is constituted by m units A arranged along the radiation direction of the incident laser beam 110. The incident laser beam 110 is attenuated by the separation of the reflected light and is incident on the next splitting unit, and this attenuation and incidence is repeated. In this way, a m parallel reflected lights A group 230 is radiated from a splitting units group A1 to Am.

Each translucent film used in the first optical system is preferred to convert 90.00 to 99.99% of the luminous energy of incident light into a transmitted light and 0.01 to 10.00% of the luminous energy into a reflected light, and is more preferred to convert 98 to 99% of the luminous energy of incident light into a transmitted light and 1 to 2% of the luminous energy into a reflected light. When the proportions of the transmitted light and the reflected light are in the above ranges, the luminous energy of the transmitted light (laser beam) incident on the last splitting unit Am is secured at a sufficient level. As a result, there are obtained, in all the splitting units, reflected lights each having a luminous energy necessary for the measurement of surface plasmon resonance phenomenon.

Figure 5:
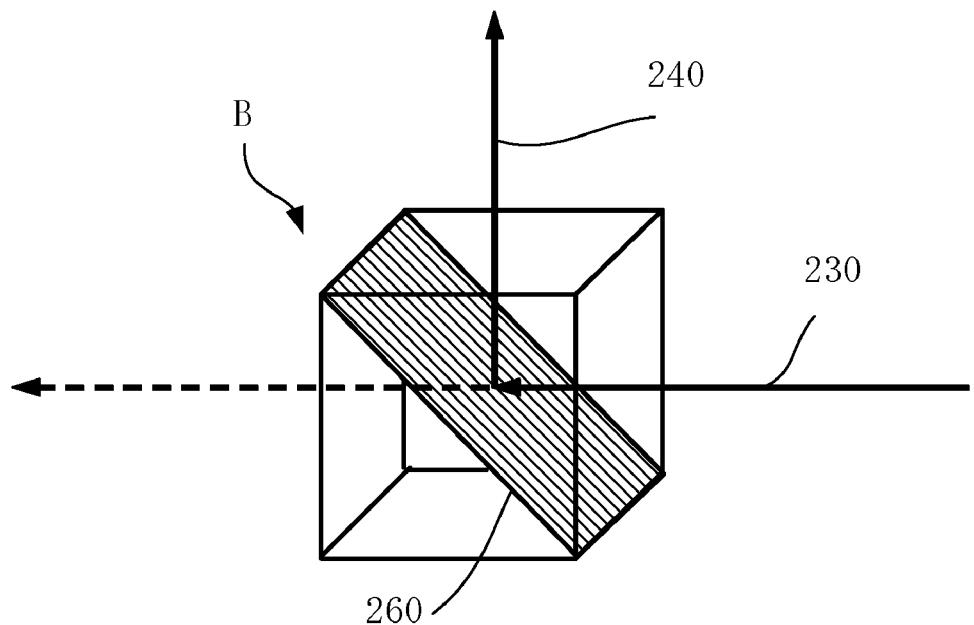
FIG. 5 is a perspective view showing an example of the splitting unit of second optical system.

FIG. 5 is a perspective showing a unit B constituting the splitting units group B11 to Bmn of second optical system 220. In FIG. 5, 260 is a translucent film which is provided along one diagonal surface of the transparent rectangular parallelepiped constituting the unit. The translucent film 260 is constituted by a film causing no optical deflection and converts part of one reflected light 230 (which is incident on the film) of parallel reflected lights A into a reflected light 240. The reflected light 230 (which is incident on the film) is attenuated owing to the partial conversion into the reflected light 240 and is incident on the next splitting unit, and this attenuation and incidence is repeated. In this way, a mn parallel reflected lights B group 240 is radiated from a splitting units group B11 to Bmn.

For the same reason as mentioned above, each translucent film used in the second optical system is preferred to convert 90.00 to 99.99% of the luminous energy of incident light into a transmitted light and 0.01 to 10.00% of the luminous energy into a reflected light, and is more preferred to convert 98 to 99% of the luminous energy of incident light into a transmitted light and 1 to 2% of the luminous energy into a reflected light.

Figure 6:
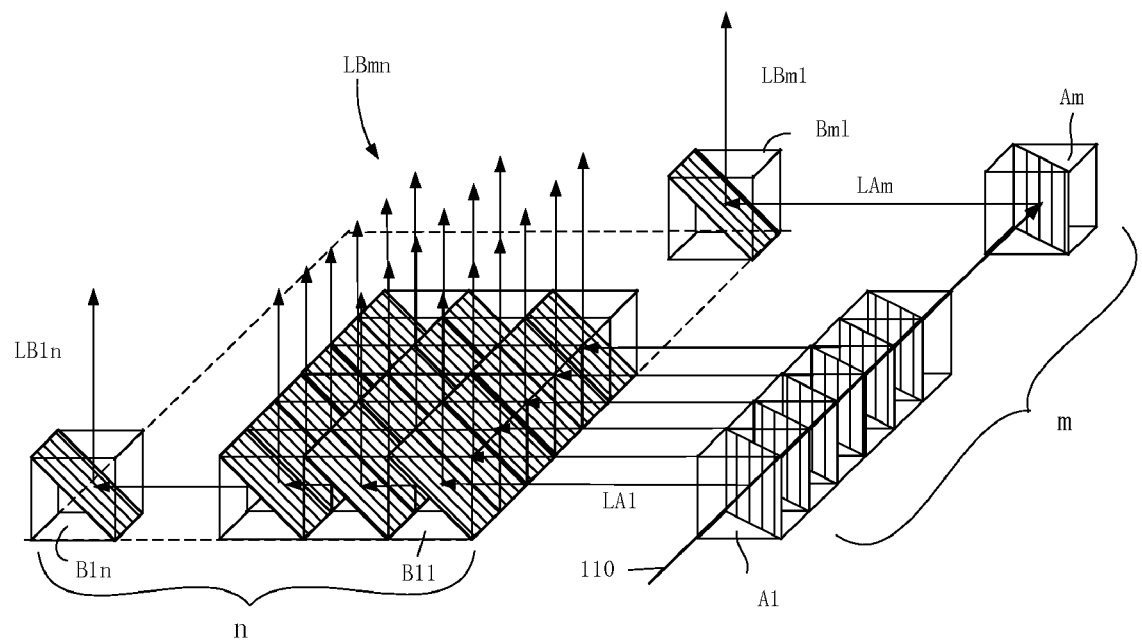
FIG. 6 is a perspective view showing an example of the arrangement of the splitting units group A of first optical system and the splitting units group B of second optical system.

FIG. 6 is a perspective view showing an example of the arrangement of the splitting units group A1 to Am of first optical system 210 (m splitting units are arranged) and the splitting units group B11 to Bmn of second optical system (m×n splitting units are arranged). In FIG. 6, LA1 is a reflected light from a splitting unit A1; LAm is a reflected light from a spitting unit Am; LB1n is a reflected light from a splitting unit B1n; LBm1 is a reflected light from a splitting unit Bm1; LBmn is a reflected lights group from a splitting units group B11 to Bmn.

Figure 7:
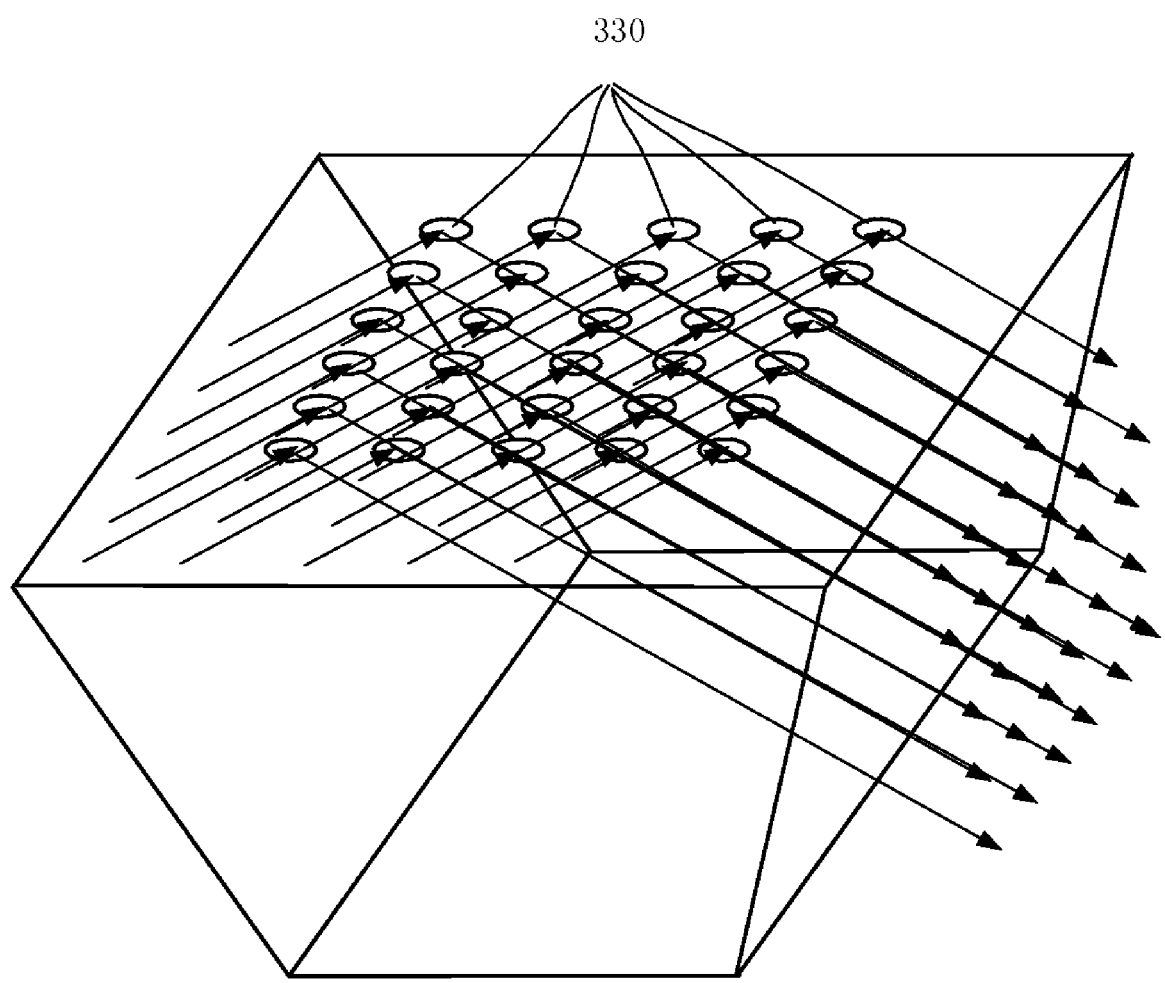
FIG. 7 is a perspective view showing an example of the arrangement of the measuring cells in sensor.

FIG. 7 is a perspective view showing an example of the arrangement of measuring cells 330 (m×n) in a sensor 300.

Figure 8:
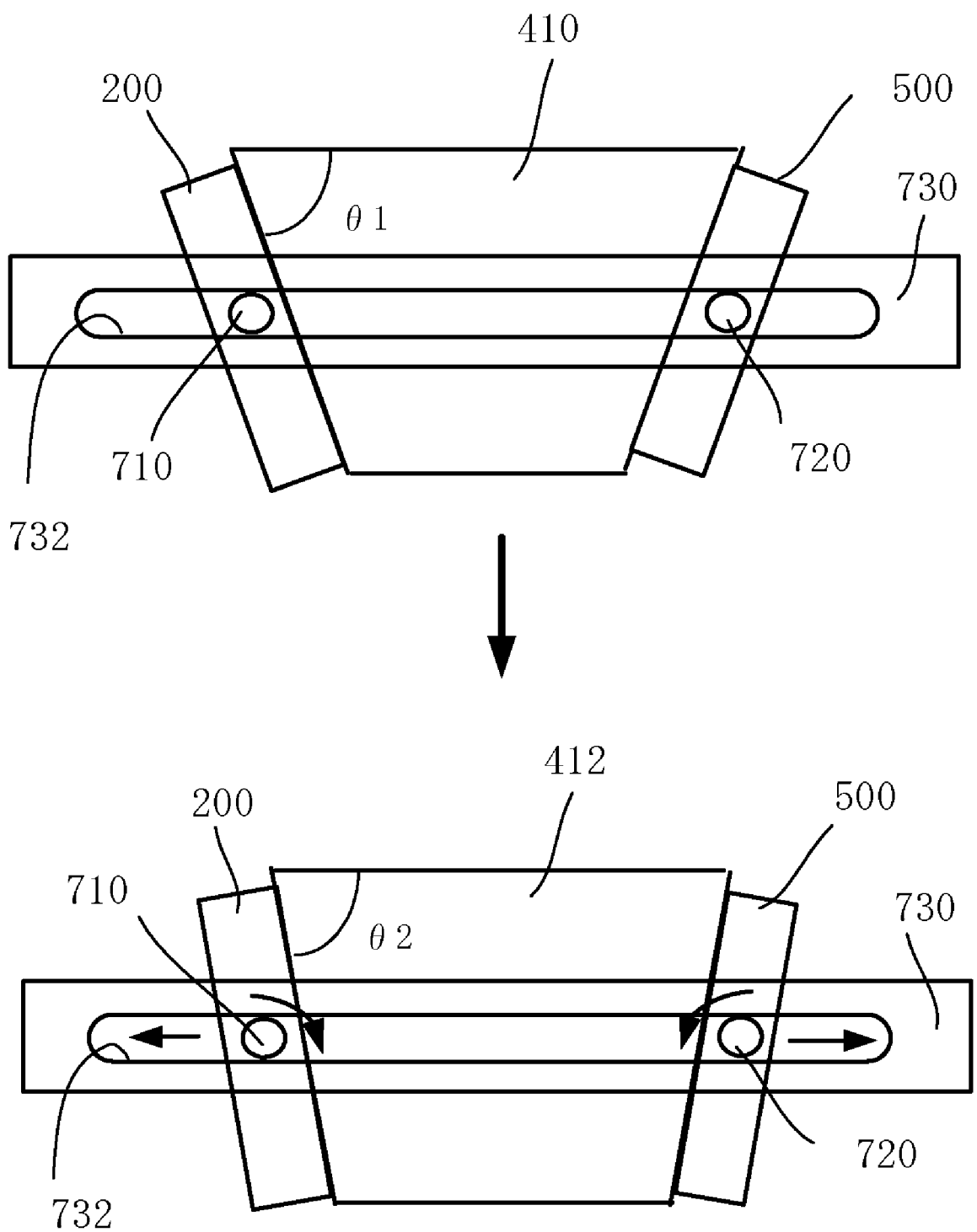
FIG. 8 is a schematic view showing an example of the mechanism for prism automatic fitting and adhesion, used for fitting a prism having an angle suitable for an intended application.

FIG. 8 is a schematic view showing an example of the mechanism for prism automatic fitting and adhesion, used for fitting a prism of different angle selected so as to be suitable for an intended application. FIG. 8 shows a way for fitting a prism when the prism 410 (used in FIG. 7) having a prism angle of θ1 is changed to a prism 412 having a prism angle of θ2 (θ1<θ2). After the change of prism, a beam splitter 200 and a detector 500 are each moved along a long hole 732 provided in a guide bar 730 and are turned about a splitter rotation axis 710 and a detector rotation axis 720, respectively, whereby the beam splitter 200 and the detector 500 are tightly adhered to the both sides of the prism 412.

Figure 9:
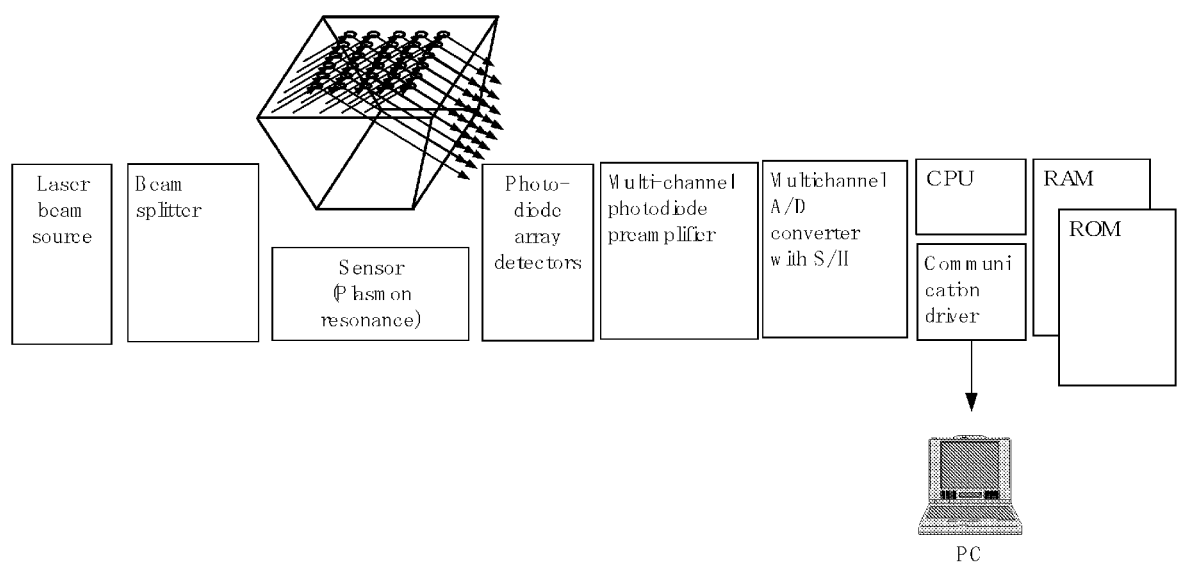
FIG. 9 is a drawing explaining a constitution of the optical system of the present invention.

FIG. 9 is a drawing explaining a constitution of the optical system of the present invention. In FIG. 9, at first, a laser beam is radiated from a light source toward a beam splitter, and a mn parallel reflected lights group is radiated from the beam splitter toward a sensor. At this time, each measuring cell in the sensor is kept in a state containing no sample, i.e. a blank state. The mn reflected lights group from the measuring cells of sensor are radiated on a photodiode array detectors group, and the optical data detected by the detectors pass through a multi-channel photodiode preamplifier and are converted by a multi-channel A/D converter with S/H. These data are recorded in a PC (personal computer), as data used for correction of the differences of the luminous energies arriving at individual measuring cells, caused by different light paths. Then, different samples for measurement are placed in individual measuring cells and the same operation as above is conducted to obtain optical data by the detectors. The optical data are corrected using the correction data recorded in the PC, to obtain measurement results.

Figure 10:
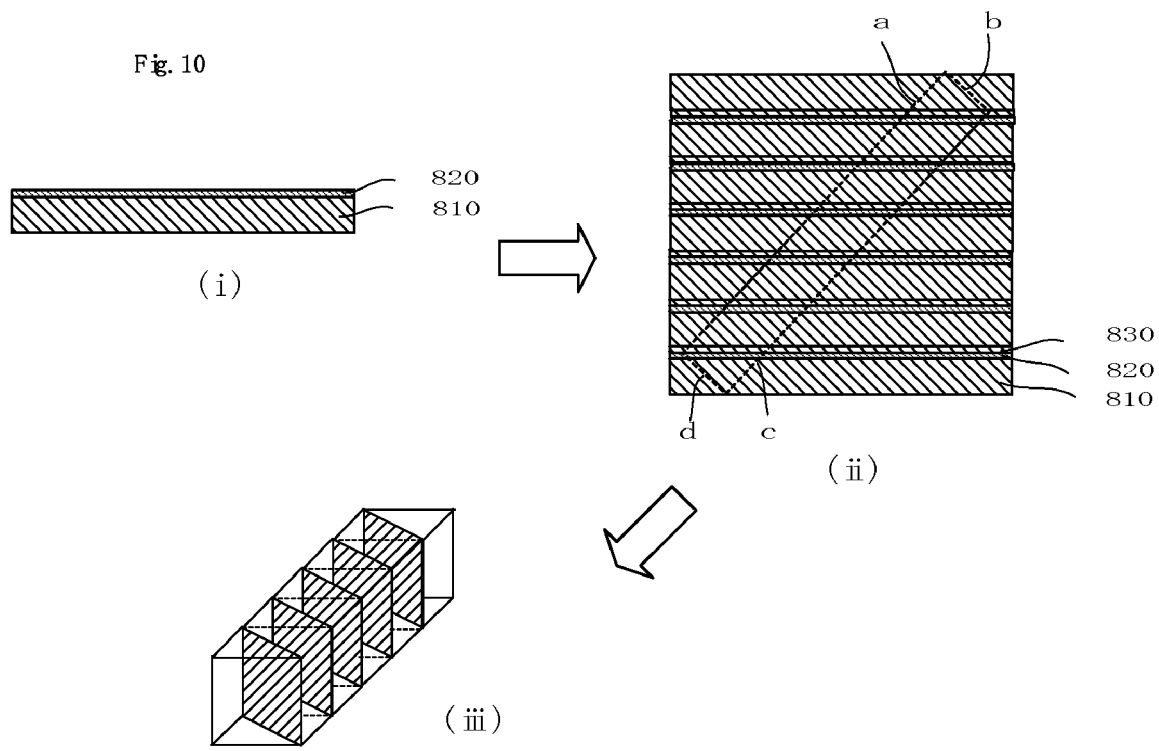
FIG. 10 is a drawing showing an example of the production steps of the splitting units of the first optical system.

FIG. 10 is a drawing showing an example of the production steps of the splitting units of first optical system. FIG. 10(i) is a sectional view of a vapor-deposited glass wherein a translucent film 820 is formed on one side of a glass plate 810 by vapor deposition. FIG. 10(ii) is a sectional view of a laminated glass (ii) obtained by laminating a plurality of the vapor-deposited glasses (i) with the vapor-deposited translucent film side of each glass (i) directed upward, using a known integration technique. In FIG. 10(ii), 830 is an adhesive layer. This laminated glass is cut at an angle of 45° relative to the surface of laminated glass, as shown by the dotted lines a to d of FIG. 10(ii), whereby a splitting units A group of first optical system, shown in a perspective view of FIG. 10(iii) can be produced. The splitting units A group is shown also in FIG. 6 as a splitting units group (A1 to Am) of first optical group.

Figure 11:
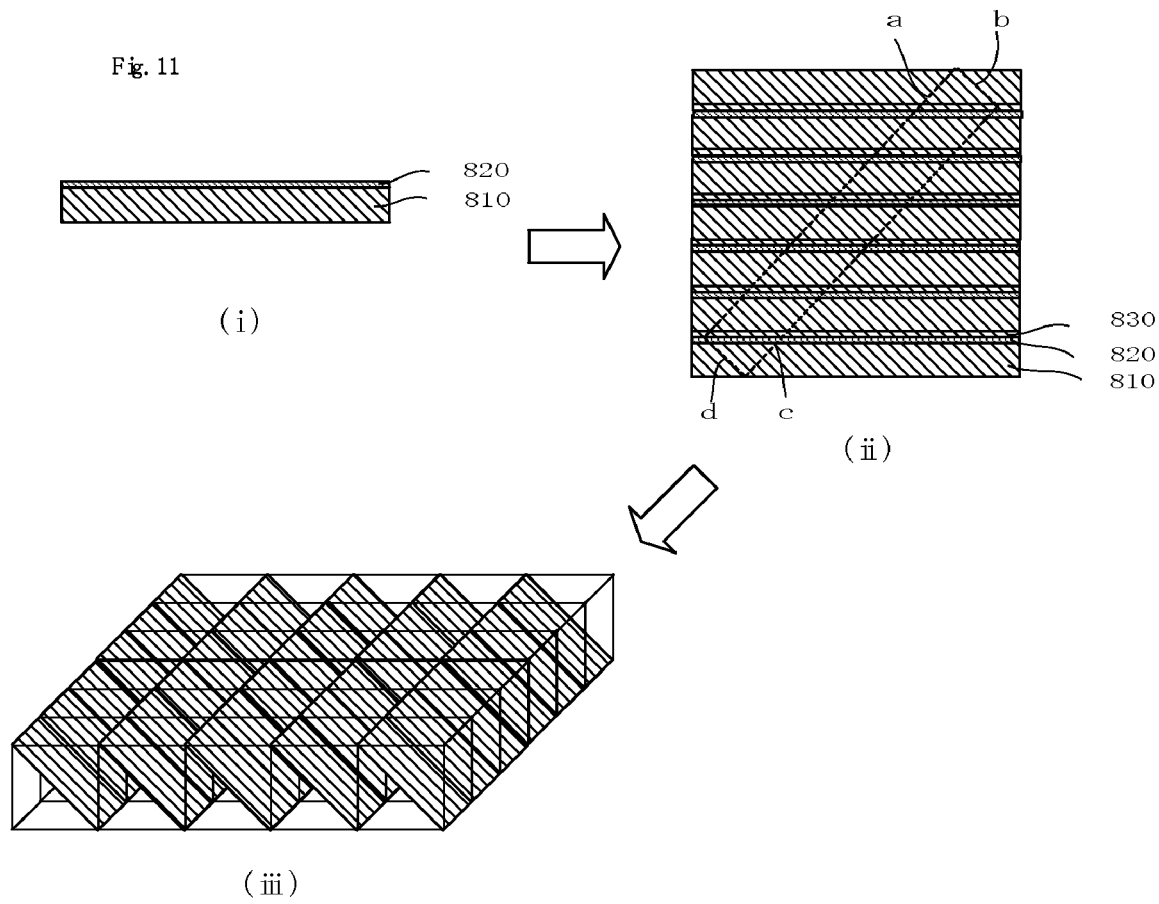
FIG. 11 is a drawing showing an example of the production steps of the splitting units of the second optical system.

FIG. 11 is a drawing showing an example of the production steps of the splitting units of second optical system. As in the case of FIG. 10, FIG. 11(i) is a sectional view of a vapor-deposited glass and FIG. 11(ii) is a sectional view of a laminated glass. This laminated glass is cut at an angle of 45° relative to the surface of laminated glass, as shown by the dotted lines a to d of FIG. 11(ii), whereby a splitting units B group of the second optical system, shown in a perspective view of FIG. 11(iii) can be produced.

As shown in FIGS. 11(i) to (iii), a wide vapor-deposited glass (i) is required when the splitting units B group is produced. The splitting units B group is shown also in FIG. 6 as a splitting units group (B11 to B1n ... Bm1 to Bmn) of second optical group.

EXAMPLES

Example 1

Example Using a Multi-channel Sensor

There is shown below an Example of 25-channel simultaneous analysis using the multi-channel surface plasmon resonance phenomenon measuring equipment of the present invention.

There were produced an optical system for multi-channel SPR, comprising a laser beam source, two multi-beam splitters, an angle-fixed trapezoidal prism, 25 rectangular photodiodes of 3×2 mm and an electric circuit, and a measurement soft ware; and a 25-channel sensor was evaluated.

The multi-beam splitters were produced as follows. That is, 7 glass plates (BK 7) of 50 mm×50 mm×1.77 mm (thickness) were prepared. On one side of each glass plate was formed a dielectric multi-layered film for adjustment of light transmittance. The formation of dielectric multi-layered film was carried out by conducting vacuum deposition using a substance containing titanium (a dielectric), as a source, and one side of each glass plate as a target, to apply multi-AR coating on the surface of glass plate. In this way, there were produced 7 light-reflecting mirrors showing a transmittance of 99% and a reflectivity of 1% to a light of 680 nm wavelength. Then, the light-reflecting mirrors were laminated to each other (the coating side of one mirror was directed upward and laminated to the non-coated side of other mirror by using a photo-curing adhesive [NOA 55 (registered trade name), a product of NOLAND Co., refractive index=1.52]), to produce a light-reflecting mirror laminate. From this light-reflecting mirror laminate were cut out splitting units.

The cut end faces of each splitting unit was polished at a profile irregularity of ⅛λ in order to obtain an increased forward movability of beam, whereby splitting units A and splitting units B were obtained.

The splitting units A and the splitting units B were arranged appropriately to produce a multi-beam splitter for laser beam, for 25-channel SPR simultaneous measurement. In the multi-beam splitter, the m and n both shown in FIG. 6 were 5 rows and 5 columns, respectively. The splitting units group A of first optical system was 12.5 mm×2.5 mm×2.5 mm in size, and the splitting units group B of second optical system was 15.5 mm×12.5 mm×2.5 mm in size. The number of the reflection surfaces of splitting units group A is 5 and the number of the reflection surfaces of splitting units group B of second optical system is 25.

Figure 12:
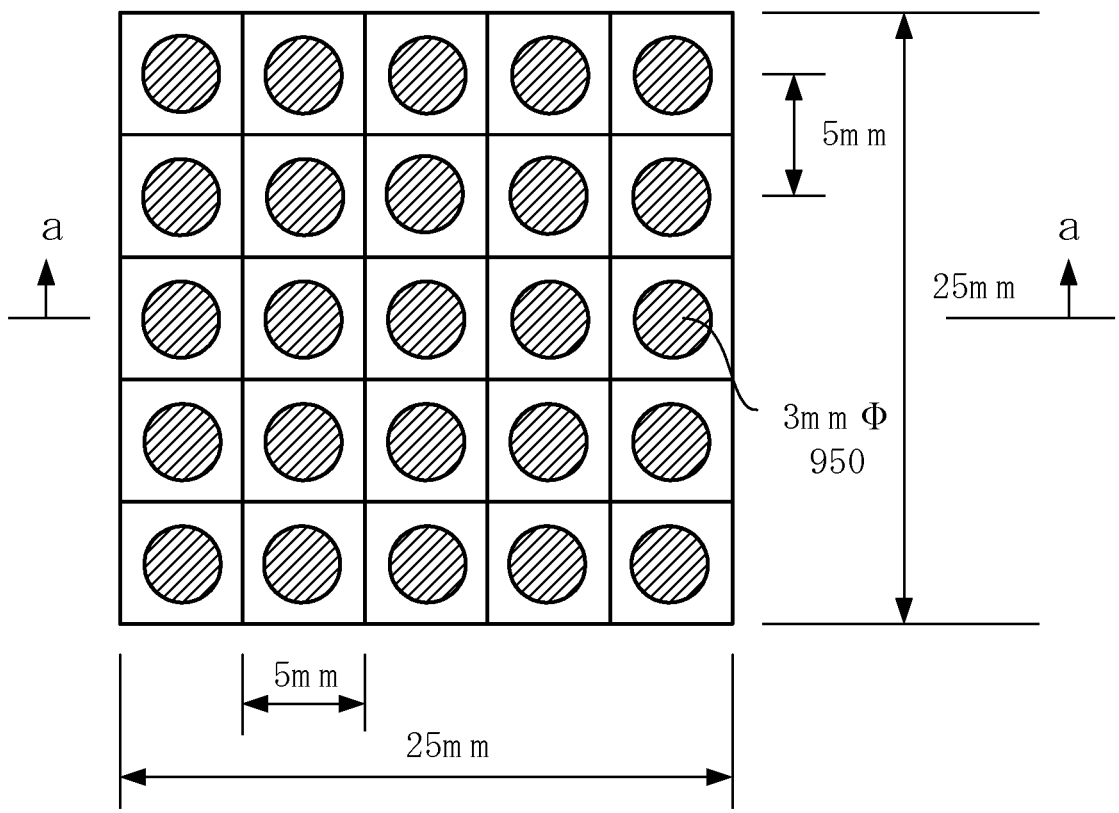
FIG. 12 is a plan view showing the structure of the 25-channel SPR sensor used in Example.
Figure 13:
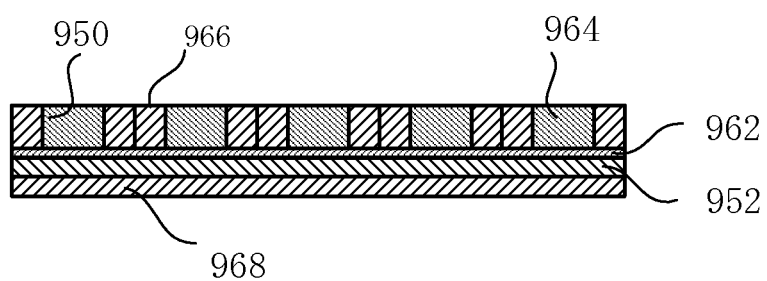
FIG. 13 is a partial sectional view taken along the a-a line of FIG. 12.

Then, the structure of the 25-channel sensor for SPR, used in the present Example is shown in FIGS. 12 and 13. FIG. 12 is a plan view of the 25-channel sensor for SPR and FIG. 13 is a sectional view taken along the a-a line of FIG. 12. In FIGS. 12 and 13, the sensor is constituted by a sensor base plate obtained by forming a vapor deposition gold film 962 of 45 nm in thickness on the upper surface of a glass plate 952 (BK 7) of 25 mm×25 mm×0.1 mm (thickness) having a refractive index of 1.5150, an adhesive silicon plate 966 (formed on the sensor base plate) of 25 mm×25 mm×1 mm (thickness) having 25-channel cells 950 (3 mm in diameter) each containing a hygroscopic resin 964 filled therein, and a PVC light interface film 968 of 0.1 mm in thickness for refractive index adjustment, which conducts light matching between the prism (BK 7) and the glass plate 952.

Figure 14:
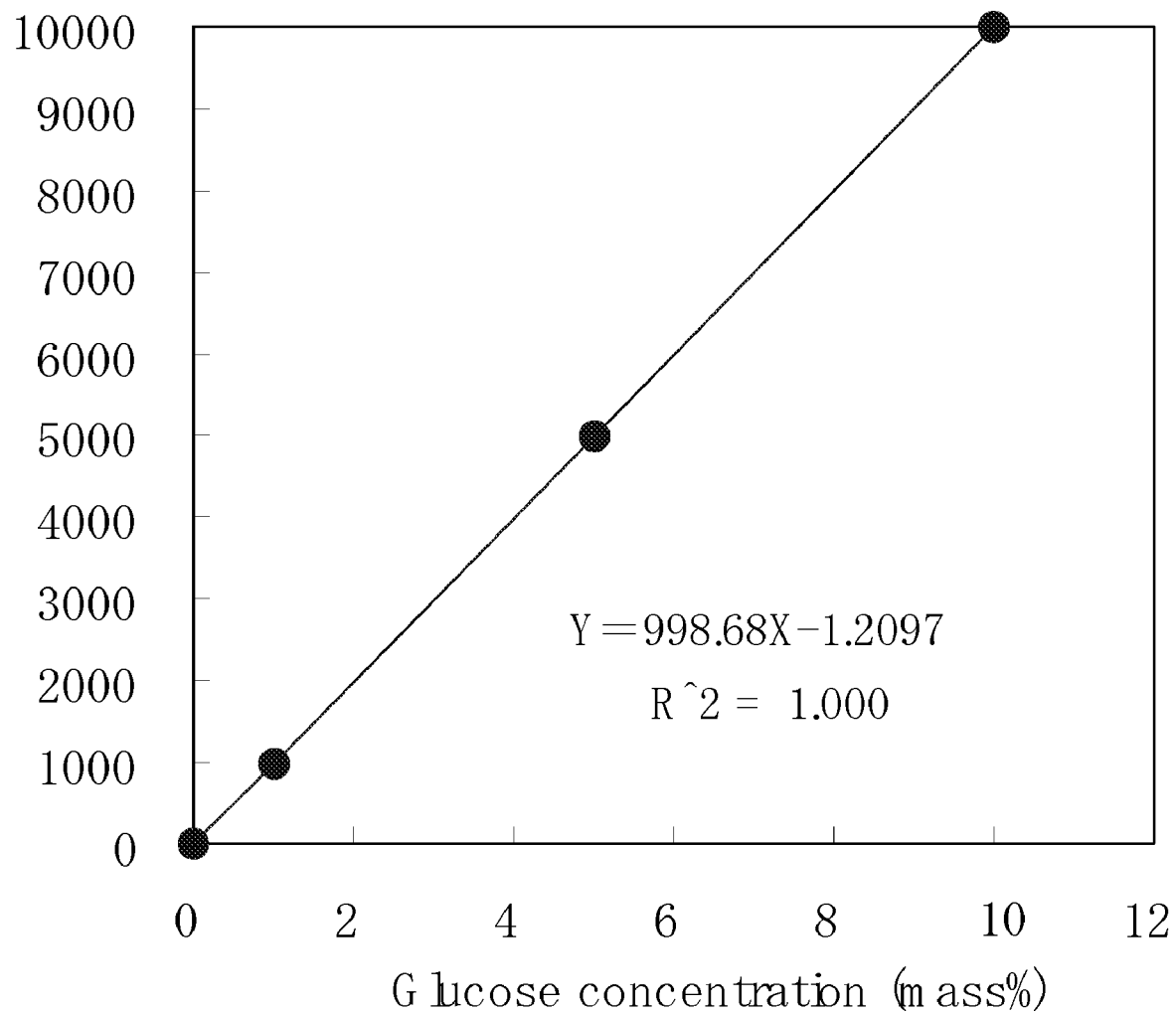
FIG. 14 is a graph showing the relation between difference in SPR intensity and concentration, obtained in Example.

In the measurement of SPR, at first, the sensor was set at a predetermined position of the prism; then, samples of different glucose concentrations ranging from 1% to 10% were placed in 21 cells in order each in an amount of 5 μl using a pipette. In the remaining 4 cells were placed pure water for reference and, as standard solutions of given glucose concentrations, aqueous glucose (1, 3 and 5%) solutions, each in the same amount. Upon pushing the measurement button of the present measurement equipment, simultaneous SPR measurement was started immediately. One minute later, there was displayed, on the screen of computer, the measurement result for each channel, of the difference between the SPR intensity of water and the SPR intensity of sample to be measured, in relation to the concentration of glucose. Part of the display and the relation between SPR intensity and concentration are shown in Table 1 and FIG. 14. As is appreciated from Table 1 and FIG. 4, the usefulness of the multi-channel surface plasmon resonance measuring equipment of the present invention is apparent and the SPR information from 25 channels agrees very well with the concentration information.

TABLE 1

| Cell No. | Differential SPR intensity | Glucose conc. (mass %) | Remarks |
|---|---|---|---|
| 1 | 10 | 0 | PBS buffer solution (pH 7.4) |
| 2 | 989 | 1 | Standard solution (prepared with PBS buffer solution) |
| 3 | 4985 | 5 | Standard solution (prepared with PBS buffer solution) |
| 4 | 9990 | 10 | Standard solution (prepared with PBS buffer solution) |
| 5 | 403 | 0.405 | Prepared sample |
| 6 | 1008 | 1.01 | " |
| 7 | 1507 | 1.51 | " |
| 8 | 2506 | 2.51 | " |
| 9 | 3195 | 3.20 | " |
| 10 | 4763 | 4.77 | " |
| 11 | 5721 | 5.73 | " |
| 12 | 6001 | 6.01 | " |
| 13 | 6320 | 6.33 | " |
| 14 | 7419 | 7.43 | " |
| 15 | 8118 | 8.13 | " |
| 16 | 8787 | 8.80 | " |
| 17 | 8917 | 8.93 | " |
| 18 | 9097 | 9.11 | " |
| 19 | 9307 | 9.32 | " |
| 20 | 9546 | 9.56 | " |
| 21 | 9646 | 9.66 | " |
| 22 | 9836 | 9.85 | " |
| 23 | 9936 | 9.95 | " |
| 24 | 10225 | 10.27 | " |
| 25 | 10535 | 10.55 | " |

Example 2

In order to clarify the applicability of the present invention to immunity measurement, there was investigated a 25-channel immunity sensor based on a IgG-antiIgG reaction. Measurement was conducted in the same manner as in Example 1 except that immunoglobulin IgG was used in place of glucose. As a result, the same result as in glucose was obtained and it has become clear that the present invention is applicable also to immunity measurement.

Therefore, the present invention has enabled palm-size, on-site, real time, multi-channel simultaneous analysis which has heretofore been impossible in conventional SPR measurement, and has made a new progress in SPR measurement field which is diversified.

In the above Examples, investigation was made with 25 channels which are small in channel number, from the standpoint of proving the effect of the present invention. However, since, in the present invention, the sensor can be made denser under the conditions that the incident lights cause no interference with each other, the sensor can be easily allowed to have more channels by preparing a microchip-like sensor with a micro-processing technique. For example, even a palm-size, 96-hole, novel ELISA equivalent can be produced easily. Further, when the sensor base plate limit of 30 mm×30 mm is exceeded under the requirement of palm size, more channels can be realized by making larger the base plate. Thus, the present invention has flexibility for the increase in number of channels. As a result, future utilization of the novel chemical analysis equipment based on the present invention is promising in fields wherein simultaneous analysis of a number of components has been needed, such as environment, agricultural chemical, food, drug, gene and the like.

The present invention can apparently contribute to the efficient resolution of various problems arising from organic substances, and the present invention is considered to be very effective in the safety of human beings and the grassroots development of bioscience in the 21st century, an age in which reliability is established based on versatile information.

The invention claimed is:

1. Surface plasmon resonance phenomenon measuring equipment comprising:
    (1) a prism,
    (2) a sensor wherein a plurality of measuring cells are formed in m rows ($m \geq 2$) and n columns ($n \geq 2$) on a metal film formed on the bottom face of the prism,
    (3) a light source for radiating a laser beam,
    (4) a first optical system wherein m optical units each having a rectangular parallelepiped shape and having a translucent film formed along the diagonal surface of the rectangular parallelepiped are arranged continuously in the direction of the laser beam radiated from the light source and thereby the laser beam is converted into a transmitted light and a m parallel reflected lights A group,
    (5) a second optical system fitted to one side of the prism, wherein optical units same as said m optical units are arranged in n columns continuously along the radiation directions of the m parallel reflected lights of said parallel reflected lights A group and thereby the parallel reflected lights A group is converted into transmitted lights and a mn parallel reflected lights group B, and wherein the reflected lights group B is radiated toward the measuring cells on the metal film formed on the bottom face of the prism, so as to hit the metal film at an incident angle including the plasmon resonance angle and thereby a reflected lights C group is radiated from other side of the prism,
    (6) a photodiode array detectors group of m rows and n columns, arranged on the extensions of the reflected lights C group, and
    (7) a polarizer interposed between a beam splitter comprising the first optical system and the second optical system and the prism, and/or between the prism and the photodiode array detectors group.

2. Surface plasmon resonance phenomenon measuring equipment according to claim 1, wherein each optical unit converts 90.00 to 99.99% of the luminous energy of the light incident thereon, into a transmitted light and 0.01 to 10.00% of the luminous energy into a reflected light.

3. Surface plasmon resonance phenomenon measuring equipment according to claim 1, which comprises an operation means for memorizing the luminous energies of reflected lights C group in blank measurement when no sample is placed in the sensor, to correct the luminous energies of reflected lights C group in sample measurement.

4. An optical apparatus for surface plasmon resonance phenomenon measuring equipment, which comprises:
    a beam splitter having:
        a first optical system wherein m optical units each having a rectangular parallelepiped shape and having a translucent film formed along the diagonal surface of the rectangular parallelepiped are arranged continuously in the direction of the laser beam radiated from the light source and thereby the laser beam is converted into a transmitted light and a m parallel reflected lights A group, and a second optical system wherein optical units same as said m optical units are arranged in n columns continuously along the radiation directions of the m reflected lights of said parallel radiated lights A group and thereby the parallel reflected lights are converted into transmitted lights and mn parallel reflected lights B group, photodiode array detectors of m rows and n columns, and a connecting member for connecting the beam splitter and the photodiode array, wherein the connecting member has a means for changing the angle and distance formed by and between the beam splitter and the photodiode.

* * * * *